(12) United States Patent
Takagi et al.

(10) Patent No.: US 6,534,683 B2
(45) Date of Patent: Mar. 18, 2003

(54) PROCESS FOR PRODUCING FLUORINATED ALKYLAMINE COMPOUND

(75) Inventors: Hirokazu Takagi, Kanagawa (JP); Keiichi Ohnishi, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/170,364

(22) Filed: Jun. 14, 2002

(65) Prior Publication Data

US 2002/0183557 A1 Dec. 5, 2002

Related U.S. Application Data

(63) Continuation of application No. PCT/JP00/08817, filed on Dec. 13, 2000.

(30) Foreign Application Priority Data

Dec. 16, 1999 (JP) ............................................ 11-357781

(51) Int. Cl.[7] ...................... C07C 209/08; C07C 211/15
(52) U.S. Cl. ....................................... 564/481; 564/482
(58) Field of Search ................................. 564/481, 482

(56) References Cited

U.S. PATENT DOCUMENTS

| 2,348,321 A | | 5/1944 | Benning et al. |
| 3,227,761 A | * | 1/1966 | De Brunner et al. ....... 260/583 |
| 4,059,629 A | * | 11/1977 | Foulletier et al. ........... 260/583 |
| 4,618,718 A | | 10/1986 | Elliott et al. |
| 5,557,017 A | | 9/1996 | Oharu et al. |
| 5,618,986 A | | 4/1997 | Oharu et al. |
| 5,648,568 A | | 7/1997 | Oharu et al. |
| 5,763,709 A | | 6/1998 | Oharu et al. |

FOREIGN PATENT DOCUMENTS

| JP | 32-3369 | 6/1957 |

OTHER PUBLICATIONS

J. B. Dickey et al., *Fluorinated Aminoanthraquinone Dyes, Industrial and Engineering Chemisry,* vol. 48, No. 2, pp. 209–213, Feb. 1956.

* cited by examiner

*Primary Examiner*—Brian Davis
(74) *Attorney, Agent, or Firm*—Oblon, Spivak, McClelland, Maier & Neustadt, P.C.

(57) ABSTRACT

$F(CF_2)_n(CH_2)_mNH_2$ is produced in high yield, while reducing the amount of by-products contained in the reaction product and preventing the reactor from corroding. Provided is a process for producing a fluorinated alkylamine compound, which comprises reacting a compound represented by $F(CF_2)_n(CH_2)_mX$ (wherein X represents a chlorine atom, a bromine atom or an iodine atom, and n and m each independently represents an integer of at least 1) with $NH_3$ to produce a compound represented by $F(CF_2)_n(CH_2)_mNH_2$ (wherein n and m have the same meanings as the above), and is characterized by conducting the reaction in the presence of a reaction solvent comprising an alkanediol as an essential component.

20 Claims, No Drawings

PROCESS FOR PRODUCING FLUORINATED ALKYLAMINE COMPOUND

This application is a Continuation of prior International Application PCT/JP00/08817, filed Dec. 13, 2000.

TECHNICAL FIELD

The present invention relates to a process for producing a fluorinated alkylamine represented by $F(CF_2)_n(CH_2)_mNH_2$.

BACKGROUND ART

A fluorinated alkylamine compound represented by $F(CF_2)_n(CH_2)_mNH_2$ is a compound useful as a starting material for the synthesis of various organic compounds. Particularly, $CF_3CH_2NH_2$ is a compound which is important as e.g. an intermediate for the synthesis of pharmaceuticals and agricultural chemicals.

As a method for producing $F(CF_2)_n(CH_2)_mNH_2$ by reacting $F(CF_2)N(CH_2)_mX$ with $NH_3$, (1) a method for producing $CF_3CH_2NH_2$ by reacting from 1 to 3 times by mol of $NH_3$ to $CF_3CH_2X$ in the presence of an inert solvent such as anhydrous N-methylpyrrolidone or anhydrous glycol (U.S. Pat. No. 4,618,718), (2) a method for producing $CF_3CH_2NH_2$ by reacting $CF_3CH_2Cl$ with concentrated aqueous ammonia, wherein from 1 to 3 times by mol of $NH_3$ is used relative to $CF_3CH_2Cl$ (U.S. Pat. No. 2,348,321) or (3) a method for producing $CF_3CH_2NH_2$ by reacting $CF_3CH_2Cl$ or $CF_3CH_2Br$ with concentrated aqueous ammonia, wherein 6.5 times by mol of $NH_3$ is used relative to $CF_2CH_2Cl$ or $CF_3CH_2Br$ (Dickey et al, Ind. Eng. Chem., Vol. 48,209, 1956), is, for example, known.

However, in the method (1), the reaction is carried out under an industrially disadvantageous high reaction pressure (7 to 11 MPa), and it is disclosed that if the pressure is lowered, the yield of $CF_3CH_2NH_2$ decreases. Further, when a duplicate test was carried out in accordance with the method (1), a problem was observed such that a part of $CF_3CH_2NH_2$ was reacted with HX formed as a by-product, to form a halogenated salt ($CF_3CH_2NH_2$•HX), whereby the yield of $CF_3CH_2NH_2$ decreased (to a level of from 70 to 87%). Further, in order to convert the formed $CF_3CH_2NH_2$•HX to $CF_3CH_2NH_2$ for recovery, it is necessary to add an aqueous alkali solution and to carry out extraction with an organic solvent, followed by distillation for purification, thus leading to a problem that the number of process steps increases, and the process becomes cumbersome. Further, there has been an additional problem that part of the formed $CF_3CH_2NH_2$ reacts with $CF_3CH_2X$ to from a secondary amine compound represented by $(CF_3CH_2)_2NH$ or a tertiary amine compound represented by $(CF_3CH_2)_3N$, whereby the yield of $CF_3CH_2NH_2$ tends to be low.

Further, in the method (2) or (3), no organic solvent is employed, and concentrated aqueous ammonia is used as a reaction solvent. $CF_3CH_2X$ is hardly soluble in concentrated aqueous ammonia, whereby the reactivity with $NH_3$ tends to be low, and a problem that the yield tends to be low, was observed. Further, when the method (2) or (3) was practically employed, it was necessary to use an expensive reactor made of a corrosion resistant material such as hastelloy, since there was a problem of corrosion of the reactor.

DISCLOSURE OF THE INVENTION

The present invention has been made to solve the above problems and provides a process for producing a fluorinated alkylamine compound, which comprises reacting a compound represented by $F(CF_2)_n(CH_2)_mX$ (wherein X represents a chlorine atom, a bromine atom or an iodine atom, and n and m each independently represents an integer of at least 1) with $NH_3$ to produce a compound represented by $F(CF_2)_n(CH_2)_mNH_2$ (wherein n and m have the same meanings as the above), and is characterized by conducting the reaction in the presence of a reaction solvent comprising an alkanediol as an essential component.

BEST MODE FOR CARRYING OUT THE INVENTION

In $F(CF_2)_n(CH_2)_mX$ in the present invention, X is preferably a chlorine atom from the viewpoint of the availability, the reactivity, etc. Further, n is preferably from 1 to 16, more preferably from 1 to 8, particularly preferably 1. m is preferably from 1 to 10, more preferably from 1 to 5, particularly preferably 1. The following compounds may be mentioned as specific examples of $F(CF_2)_n(CH_2)_mX$.

$CF_3CH_2Cl$, $CF_3CH_2Br$, $CF_3CH_2I$, $CF_3CF_2CH_2Cl$, $CF_3CF_2CH_2Br$, $CF_3CF_2CH_2I$, $F(CF_2)_3CH_2Cl$, $F(CF_2)_4CH_2Cl$, $F(CF_2)_5CH_2Cl$, $F(CF_2)_6CH_2Cl$, $F(CF_2)_7CH_2Cl$, $F(CF_2)_8CH_2Cl$.

$CF_3(CH_2)_2Cl$, $CF_3(CH_2)_2Br$, $CF_3(CH_2)_2I$, $CF_3CF_2(CH_2)_2Cl$, $CF_3CF_2(CH_2)_2Br$, $CF_3CF_2(CH_2)_2I$, $F(CF_2)_3(CH_2)_2Cl$, $F(CF_2)_4(CH_2)_2Cl$, $F(CF_2)_5(CH_2)_2Cl$, $F(CF_2)_6(CH_2)_2Cl$, $F(CF_2)_7(CH_2)_2Cl$, $F(CF_2)_8(CH_2)_2Cl$.

$CF_3(CH_2)_3Cl$, $CF_3(CH_2)_3Br$, $CF_3(CH_2)_3I$, $CF_3CF_2(CH_2)_3Cl$, $CF_3CF_2(CH_2)_3Br$, $CF_3CF_2(CH_2)_3I$, $F(CF_2)_4(CH_2)_3Cl$, $F(CF_2)_4(CH_2)_3Cl$, $F(CF_2)_5(CH_2)_3Cl$, $F(CF_2)_6(CH_2)_3Cl$, $F(CF_2)_7(CH_2)_3Cl$, $F(C F_2)_8(CH_2)_3Cl$.

In the present invention, at the time of reacting $F(CF_2)_n(CH_2)_mX$ with $NH_3$, a solvent comprising an alkanediol as an essential component, is used. As the alkanediol, a $C_{2-10}$ alkanediol is preferred for the reason of handling efficiency and the physical properties of the solvent. Further, as such an alkanediol, octane-1,8-diol, propylene glycol or ethylene glycol is preferred. Further, propylene glycol or ethylene glycol is particularly preferred, since the effects of the present invention are thereby distinctly observed.

Further, the reaction solvent preferably consists essentially of an alkanediol or essentially of an alkanediol and water. Particularly preferred is a reaction solvent consisting essentially of at least one member selected from propylene glycol and ethylene glycol, or a reaction solvent consisting essentially of at least one member selected from propylene glycol and ethylene glycol, and water. Especially preferred is a reaction solvent consisting of at least one member selected from propylene glycol and ethylene glycol. When water is present in the solvent, the total amount of the alkanediol is preferably at least 1 mass %, more preferably at least 10 mass %, relative to water.

The alkanediol is believed to have an activity to increase the solubility of $F(CF_2)_n(CH_2)_mX$ and the reactivity of $NH_3$ with $F(CF_2)_n(CH_2)_mX$. If the proportion of the alkanediol in the reaction solvent becomes large, there will be an effect such that the yield of the fluorinated alkylamine compound will be remarkably high. Further, by using the alkanediol, $F(CH_2)_n(CH_2)_mNH_2$ will be formed in high yield even when the reaction pressure is adjusted to be low. Further, corrosion of the reactor can be prevented by using the alkanediol.

If the amount of the reaction solvent is too much, the volume efficiency of the reactor tends to be poor, and there will be a drawback that the productivity decreases. On the other hand, if the amount of the reaction solvent is too small, $NH_3$ and $F(CF_2)_n(CH_2)_mX$ tend not to sufficiently be dissolved in the reaction solvent, whereby an industrially disadvantageous high reaction pressure will have to be used. Accordingly, the amount of the reaction solvent is preferably from 0.5 to 50 times by mass, more preferably from 1 to 20 times by mass, relative to $F(CF_2)_n(CH_2)_mX$.

In the present invention, at the time of reacting $F(CF_2)_n(CH_2)_mX$ with $NH_3$, it is preferred to employ at least 4 times by mol of $NH_3$ relative to $F(CF_2)_n(CH_2)_mX$. Namely, HX as a by-product (HX) in the reaction of $F(CF_2)_n(CH_2)_mX$ with $NH_3$, will further react with $NH_3$ to form $NH_4X$, but if the amount of $NH_3$ is small, HX will also react with $F(CF_2)_n(CH_2)_mNH_2$ to form $F(CF_2)_n(CH_2)_mNH_2 \cdot HX$. However, by adjusting the amount of $NH_3$ to be at least a certain specific level, the amount of formation of $F(CF_2)_n(CH_2)_mNH_2 \cdot HX$ can be remarkably reduced. This is considered to be such that excessively present $NH_3$ has a function to convert $F(CF_2)_n(CH_2)_mNH_2 \cdot HX$ to $F(CF_2)_n(CH_2)_mNH_2$.

On the other hand, if the amount of $NH_3$ is too much, the reaction pressure will be high, and there will be a problem such that unreacted $NH_3$ will remain, or the operation efficiency and economical efficiency tend to be low. From the foregoing reasons, the amount of $NH_3$ is more preferably from 4 to 10 times by mol, particularly preferably from 4 to 6 times by mol, relative to $F(CF_2)_n(CH_2)_mX$.

Further, it is considered that if $NH_3$ is present excessively, $NH_3$ will also suppress a side reaction to form a secondary amine compound or a tertiary amine compound. Further, the alkanediol to be used as the reaction solvent, is considered to suppress such a side reaction by promoting the reaction of $F(CF_2)_n(CH_2)_mX$ with $NH_3$.

In the reaction of the present invention, the reaction temperature is preferably from 30 to 250° C., more preferably from 150 to 250° C., particularly preferably from 170 to 210° C. The reaction temperature may not necessarily be constant and may preferably be changed as the case requires.

Further, it is preferred that the reaction pressure is suitably changed by adjusting the supply ratio of the reaction solvent and $F(CF_2)_n(CH_2)_mX$. Usually, it is preferably from 0.5 to 10 MPa (gauge pressure, hereinafter represented by a gauge pressure, unless otherwise specified), more preferably from 0.5 to 5 MPa, particularly preferably from 1 to 5 MPa, most preferably from 1 to 3 MPa. If the amount of the reaction solvent is large, the reaction pressure decreases, and if it is small, the reaction pressure increases. Further, if the reaction pressure is too high, such is disadvantageous from the viewpoint of the operation efficiency and capital investment, and if it is too low, no adequate reaction rate tends to be obtained. In the present invention, the product can be obtained in good yield even under low pressure, by using the alkanediol as the solvent By the reaction of the present invention, a fluorinated alkylamine compound represented by $F(CF_2)_n(CH_2)_mNH_2$ is formed. In the compound, n and m are the same as n and m in the starting material. The following compounds may be mentioned as specific examples of the fluorinated alkylamine compound.

$CF_3CH_2NH_2$, $CF_3CF_2CH_2NH_2$, $F(CF_2)_3CH_2NH_2$, $F(CF_2)_4CH_2NH_2$, $F(CF_2)_5CH_2NH_2$, $F(CF_2)_6CH_2NH_2$, $F(CF_2)_7CH_2NH_2$, $F(CF_2)_8CH_2NH_2$.

$CF_3(CH_2)_2NH_2$, $CF_3CF_2(CH_2)_2NH_2$, $F(CF_2)_3(CH_2)_2NH_2$, $F(CF_2)_4(CH_2)_2NH_2$, $F(CF_2)_5(CH_2)_2NH_2$, $F(CF_2)_6(CH_2)_2NH_2$, $F(CF_2)_7(CH_2)_2NH_2$, $F(CF_2)_8(CH_2)_2NH_2$.

$CF_3(CH_2)_3NH_2$, $CF_3CF_2(CH_2)_3NH_2$, $F(CF_2)_3(CH_2)_3NH_2$, $F(CF_2)_4(CH_2)_3NH_2$, $F(CF_2)_5(CH_2)_3NH_2$, $F(CF_2)_6(CH_2)_3NH_2$, $F(CF_2)_7(CH_2)_3NH_2$, $F(CF_2)_8(CH_2)_3NH_2$.

The reaction of the present invention is carried out preferably by introducing the reaction solvent, $F(CF_2)_n(CH_2)_mX$ and $NH_3$ into a reactor by a batch system or a continuous system and dissolving the compounds in the reaction system in the reaction solvent. The timing for introducing $NH_3$ and $F(CF_2)_n(CH_2)_mX$ is not particularly limited, and a method of charging all the amounts all at once preliminarily before the reaction, a method of continuously supplying them during the reaction, or a method of dividedly supplying them during the reaction, may, for example, be mentioned.

Further, at the initial stage of the reaction, the reaction may be carried out by a small amount of $NH_3$, and at the final stage of the reaction, the reaction may be carried out by supplying a large amount of $NH_3$. Here, if the amount of $NH_3$ used at the initial stage of the reaction is small, $(CF_2)_n(CH_2)_mNH_2 \cdot HX$ may be formed, but even in such a case, by supplying $NH_3$ in a large amount at the final stage of the reaction, it is possible to reduce the amount of formation of $F(CF_2)_n(CH_2)_mNH_2 \cdot HX$ and increase the yield of the desired compound.

In the reaction of the present invention, the conversion and selectivity are high, whereby a reaction crude product containing the fluorinated alkylamine compound obtained by the reaction can be made to be a fluorinated alkylamine compound of high purity by a simple purification operation. For example, by subjecting the reaction crude product to purification by distillation as it is, it is possible to recover $F(CF_2)_n(CH_2)_mNH_2$ of high purity. At the time of the distillation, it is preferred to maintain the condenser temperature to a level lower by at least 10° C. than the boiling point of $F(CF_2)_n(CH_2)_mNH_2$ in order to prevent a decrease in the recovery rate by discharge of $F(CF_2)_n(CH_2)_mNH_2$ together with $NH_3$. Further, the pressure during the distillation is preferably adjusted to be at least 0.1 MPa (absolute pressure).

The fluorinated alkylamine compound is a compound useful as a starting material for the synthesis of various organic compounds. For example, $CF_3CH_2NH_2$ is a compound which is important as an intermediate for the synthesis of therapeutic agents for osteoporosis, cancer, etc., or as an intermediate for the synthesis of agricultural chemicals.

EXAMPLES

Now, specific embodiments of the present invention will be described in detail with reference to Examples. However, the present invention is by no means restricted thereto. The analysis of products was carried out by gas chromatography (GC) and $^{19}$F-NMR, and the ratios of components in Table 1 are values converted to mol %. Further, the ratio of other components in Table 1 was calculated by using a mol factor of $CF_3CH_2Cl$.

Example 1

Into a pressure stirring type autoclave made of stainless steel and having a capacity of 200 ml, 0.15 mol of $CF_3CH_2Cl$, 0.4 mol (2.7 times by mol relative to $CF_3CH_2Cl$) of anhydrous ammonia and 0.8 mol (5.3 times by mol relative to $CF_3CH_2Cl$) of propylene glycol, were charged and stirred at 180° C. for 48 hours to carry out the reaction. The pressure in the autoclave was initially 1.2 MPa, but decreased to 1.0 MPa at the termination. After the termination of the reaction, the autoclave was cooled to 120° C., and the gas component in the autoclave was purged via a condenser, and the gas component containing $CF_3CH_2NH_2$ was collected by a cooling trap. On the other hand, in the autoclave, 100 g of water was added to have the residual substances dissolved, and the internal standard was added to the dissolved substances, whereupon $^{19}$F-NMR was measured to quantitatively analyze $CF_3CH_2NH_2 \cdot HX$. The substances collected by the cooling trap and the content of the autoclave were analyzed, and the results are shown in Table 1. After the reaction, no substantial corrosion of the reactor was observed.

Example 2

The reaction was carried out in the same manner as in Example 1 except that anhydrous ammonia was increased to 0.6 mol (4.0 times by mol relative to $CF_3CH_2Cl$). The reaction pressure was initially 2.0 MPa, but decreased to 1.5 MPa at the termination. Products were analyzed, and the results are shown in Table 1. After the reaction, no corrosion of the reactor was observed.

Example 3

Into a pressure stirring type autoclave made of stainless steel and having a capacity of 200 ml, 0.15 mol of $CF_3CH_2Cl$, 0.6 mol (4 times by mol relative to $CF_3CH_2Cl$) of anhydrous ammonia, and 1.2 mols (8 times by mol relative to $CF_3CH_2Cl$) of propylene glycol, were charged, and stirred at 200° C. for 48 hours to carry out the reaction. The pressure in the autoclave was 2.2 MPa at the initial stage of the reaction, but decreased to 1.7 MPa at the termination of the reaction. After termination of the reaction, the autoclave was cooled to 120° C., and the gas component in the autoclave was purged via a condenser, and the gas component containing $CF_3CH_2NH_2$ was collected by a cooling trap. The substances collected by the cooling trap and the content of the autoclave were analyzed, and the results are shown in Table 1. After the reaction, no substantial corrosion of the reactor was observed.

Example 4

Into a pressure stirring type autoclave made of stainless steel and having a capacity of 2,000 ml, 1.5 mols of $CF_3CH_2Cl$, 6 mols (4 times by mol relative to $CF_3CH_2Cl$) of anhydrous ammonia, and 12 mols (8 times by mol relative to $CF_3CH_2Cl$) of propylene glycol, were charged and stirred at 200° C. for 48 hours to carry out the reaction. The reaction pressure was initially 2.2 MPa, but decreased to 1.7 MPa at the termination. After termination of the reaction, the autoclave was cooled to 10° C. The reaction crude product recovered from the autoclave was analyzed. As a result, the conversion was 97.5%, and the selectivity for $CF_3CH_2NH_2$ was 97.8%. Further, the reaction crude product was subjected to purification by distillation under atmospheric pressure at −20° C. (the condenser temperature) to obtain a fraction. The fraction was analyzed, and the results are shown in Table 1. After the reaction, no substantial corrosion of the reactor was observed.

Example 5

The reaction was carried out in the same manner as in Example 3 by changing 1.2 mols of propylene glycol to 1.2 mols of ethylene glycol. The reaction pressure was initially 2.1 MPa, but decreased to 1.6 MPa at the termination. The products were analyzed, and the results are shown in Table 1. After the reaction, no corrosion of the reactor was observed.

TABLE 1

|  | Example | | | | |
|---|---|---|---|---|---|
|  | 1 | 2 | 3 | 4 | 5 |
| Reaction temperature (° C.) | 180 | 180 | 200 | 200 | 200 |
| $NH_3/CF_3CH_2Cl$ ratio (molar ratio) | 2.7 | 4.0 | 4.0 | 4.0 | 4.0 |
| Conversion of $CF_3CH_2Cl$ (%) | 90.4 | 90.5 | 97.5 | 97.5 | 93.2 |
| Composition of products (mol %) | | | | | |
| $CF_3CH_3$ | 0.3 | 0.8 | 0.8 | 0.0 | 3.2 |
| $CF_3CH_2NH_2$ | 95.2 | 97.8 | 97.8 | 99.8 | 93.8 |
| $CF_3CH_2NH_2 \cdot HX$ | 2.2 | 0.0 | 0.0 | 0.0 | 0.0 |
| $(CF_3CH_2)_2NH$ | 2.0 | 1.0 | 1.1 | 0.1 | 2.3 |
| Others | 0.3 | 0.4 | 0.3 | 0.1 | 0.7 |

INDUSTRIAL APPLICABILITY

According to the present invention, by using a reaction solvent comprising an alkanediol as an essential component, the desired fluorinated alkylamine compound can be produced in high yield, while reducing the amount of by-products in the reaction product and preventing the reactor from corroding. Further, even if the reaction pressure is adjusted to be low, the desired fluorinated alkylamine compound can be obtained in adequate yield.

The entire disclosure of Japanese Patent Application No. 11-357781 filed on Dec. 16, 1999 including specification, claims and summary are incorporated herein by reference in its entirety.

What is claimed is:

1. A process comprising
reacting a compound represented by formula $$F(CF_2)_n(CH_2)_mX$$

with $NH_3$ to produce a compound represented by formula $$F(CF_2)_n(CH_2)_mNH_2,$$

wherein X is a chlorine atom, a bromine atom or an iodine atom, and n and m are each independently an integer of at least 1,
wherein the reaction is conducted in the presence of a reaction solvent comprising an alkanediol, and
wherein $NH_3$ is present in an amount of at least 4 times by mol relative to $F(CH_2)_n(CH_2)_mX$.

2. The process according to claim 1, wherein the alkanediol is a $C_{2-10}$ alkanediol.

3. The process according to claim 1, wherein the alkanediol is ethylene glycol, propylene glycol or a mixture thereof.

4. The process according to claim 1, wherein n is 1, and m is 1.

5. The process according to claim 1, wherein the reaction solvent consists essentially of an alkanediol.

6. The process according to claim 1, wherein X is a chlorine atom.

7. The process according to claim 1, wherein the reaction pressure is from 0.5 to 10 MPa.

8. The process according to claim 1, wherein the reaction pressure is from 1 to 5 MPa.

9. The process according to claim 1, further comprising distilling a reaction crude product formed by the reaction to obtain a purified fluorinated alkylamine compound.

10. The process according to claim 1, wherein the $NH_3$ is present in an amount of from 4 to 10 times by mol relative to the amount of $F(CF_2)_n(CH_2)_mX$.

11. A process comprising reacting a compound represented by $$F(CF_2)_n(CH_2)_mX$$

with $NH_3$ to produce a compound represented by $$F(CF_2)_n(CH_2)_mNH_2,$$

wherein X is a chlorine atom, a bromine atom or an iodine atom, and n and m are each independently an integer of at least 1, and wherein the reaction is conducted in the presence of a reaction solvent comprising an alkanediol and water.

12. The process according to claim 11, wherein the alkanediol is a $C_{2-10}$ alkanediol.

13. The process according to claim 11, wherein the alkanediol is ethylene glycol, propylene glycol or a mixture thereof.

14. The process according to claim 11, wherein the reaction solvent consists essentially of an alkanediol and water.

15. The process according to claim 11, wherein X is a chlorine atom.

16. The process according to claim 11, wherein the reaction pressure is from 0.5 to 10 MPa.

17. The process according to claim 11, wherein the reaction pressure is from 1 to 5 MPa.

18. The process according to claim 11, further comprising distilling a reaction crude product formed by the reaction to obtain a purified fluorinated alkylamine compound.

19. The process according to claim 11, wherein n is 1 and m is 1.

20. The process according to claim 11, wherein the $NH_3$ is present in an amount of 4 to 10 times by mol relative to the amount of $F(CF_2)_n(CH_2)_mX$.

* * * * *